(12) United States Patent
Mirda (10) Patent No.: US 9,763,695 B2
(45) Date of Patent: Sep. 19, 2017

(54) SPINAL IMPLANT SYSTEM AND METHOD

(71) Applicant: Warsaw Orthopedic, Inc., Warsaw, IN (US)

(72) Inventor: James M. Mirda, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 79 days.

(21) Appl. No.: 14/541,900

(22) Filed: Nov. 14, 2014

(65) Prior Publication Data

US 2016/0135846 A1 May 19, 2016

(51) Int. Cl.
*A61B 17/70* (2006.01)

(52) U.S. Cl.
CPC ........ *A61B 17/7004* (2013.01); *A61B 17/705* (2013.01); *A61B 17/7055* (2013.01)

(58) Field of Classification Search
CPC ............ A61B 17/7049; A61B 17/7055; A61B 17/7058; A61B 17/7059; A61B 17/7061
USPC .......................... 606/246, 250–253, 260, 278
See application file for complete search history.

(56) References Cited

U.S. PATENT DOCUMENTS 8,337,527 B2 * 12/2012 Hawkins .............. A61B 17/705
606/151
2004/0153070 A1 * 8/2004 Barker ............... A61B 17/7055
606/281

* cited by examiner

*Primary Examiner* — Ellen C Hammond
*Assistant Examiner* — Christina Negrellirodrigue (57) ABSTRACT

A spinal construct comprises a fastener attachable with sacral and/or pelvic tissue of a body. At least one connector is connected with the fastener and defines a first implant cavity and a second implant cavity. At least one lock is disposable with the implant cavities. Systems and methods are disclosed.

20 Claims, 4 Drawing Sheets

SPINAL IMPLANT SYSTEM AND METHOD

TECHNICAL FIELD

The present disclosure generally relates to surgical implants for the treatment of spinal disorders, and more particularly to a surgical system and method for treatment of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods, connectors and plates can be used to provide stability to a treated region. During surgical treatment, one or more rods may be attached via fasteners and connectors to the exterior of two or more vertebral members to provide stability to a treated region. Fasteners may also be attached to iliac bone. This disclosure describes an improvement over these prior art technologies.

SUMMARY

In one embodiment, a spinal construct is provided. The spinal construct comprises a fastener attachable with sacral and/or pelvic tissue of a body. At least one connector is connected with the fastener and defines a first implant cavity and a second implant cavity. At least one lock is disposable with the implant cavities. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present disclosure provides a surgical system including a spinal construct having one or more lateral, offset and/or iliac connectors configured to facilitate use with one or more spinal rods. In one embodiment, the spinal construct includes a connector employed with a plurality of implants, such as, for example, three, four, five and/or more spinal rods disposed adjacent to each other within the spinal construct. In some embodiments, the spinal construct may be employed with a surgical procedure, such as, for example, a pedicle subtraction osteotomy (PSO), tumor, trauma and/or treatment of an adult degeneration and/or deformity. In some embodiments, the spinal construct includes components that transverse thoracolumbar (TL) or the lumbosacral spine (LS) junctions.

In some embodiments, the present disclosure provides a surgical system including a spinal construct having a connector configured for disposal of multiple spinal rods. In some embodiments, the present disclosure provides a surgical system including a spinal construct disposed such that one Iliac screw is attached to an iliac connector and includes two openings, such as, for example, eyelets to receive two spinal rods. In some embodiments, this configuration reduces the number of construct components, reduces time, and reduces patient exposure.

In some embodiments, the spinal construct is configured for disposal of various spinal rod diameters. In one embodiment, the surgical system includes a spinal construct including a closed/closed posted connector that utilizes set screws to lock the spinal rods in place. In one embodiment, the surgical system includes a spinal construct employed with a PSO surgical procedure such that outrigger rods are disposed adjacent to existing spinal rods and the outrigger rods extend to two iliac screws positioned superior/inferior to each other. In one embodiment, each spinal rod is connected with a dedicated connector that extends to a dedicated iliac screw.

In one embodiment, the surgical system includes a spinal construct having a connector that facilitates the disposal of two spinal rods uni-laterally with only one Iliac screw. In one embodiment, the surgical system includes a spinal construct that is disposed with vertebrae in a bi-lateral orientation.

In some embodiments, the surgical system includes a spinal construct having one or more connectors utilized as a longitudinal rod. In some embodiments, the surgical system includes a spinal construct having four connectors utilized as longitudinal rods. In one embodiment, the surgical system includes a spinal construct employed with a tumor and/or trauma application, such as, for example, a partial and/or full sacrectomy such that two trans-sacral rods extend to the iliac screws and the longitudinal rods connect the construct with the screws.

In one embodiment, the surgical system includes a spinal construct comprising a connector having various geometries, such as, for example, closed/closed, closed/open, open/open, closed/side load and open/side load. In one embodiment, the surgical system includes a connector having a post with various diameters, such as, for example, 4.5 millimeters (mm), 4.75 mm, 5.0 mm, 5.5 mm, 6.0 mm or 6.35 mm. In one embodiment, the surgical system includes a connector having a post with various lengths, such as, for example, in a range of 10 mm through 60 mm or greater. In one embodiment, the surgical system includes a connector having openings that receive spinal rods, the openings being disposable in range of offset orientations. In one embodiment, the surgical system includes a connector having a lock, such as, for example, a set screw. In one embodiment, the surgical system includes a spinal construct comprising a multiple rod construct. In one embodiment, the surgical system includes a spinal construct comprising a multiple rod construct disposed in a uni-lateral configuration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Figure 1:
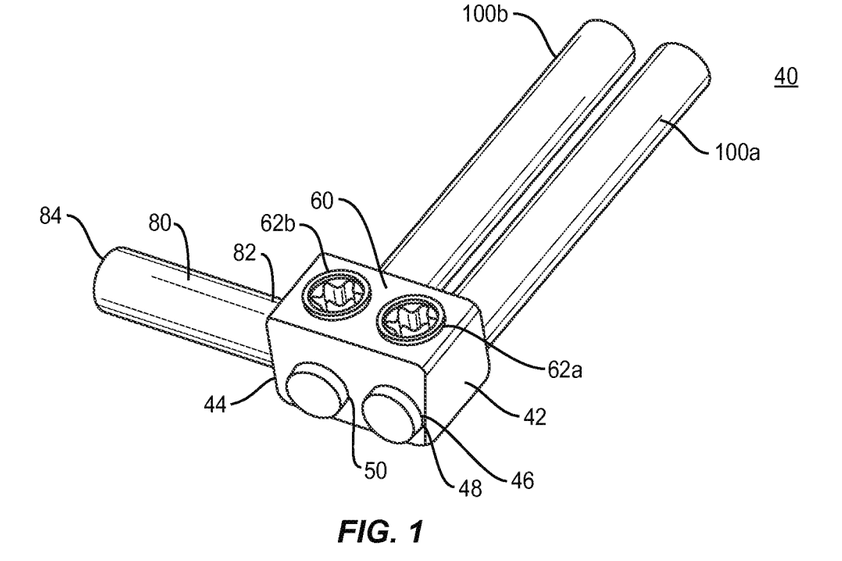
FIG. 1 is a perspective view of components of one embodiment of a system in accordance with the principles of the present disclosure.
Figure 2:
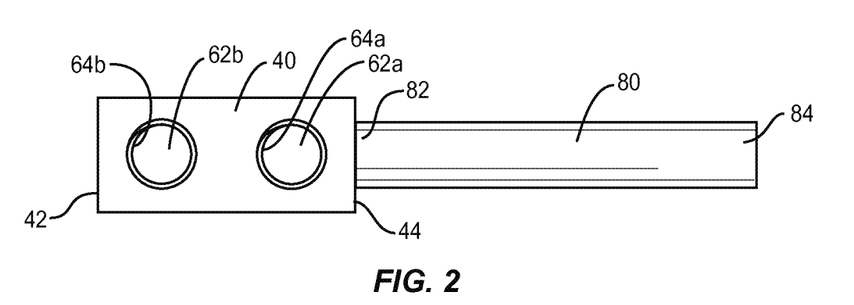
FIG. 2 is a side view of the components shown in FIG. 1.
Figure 3:
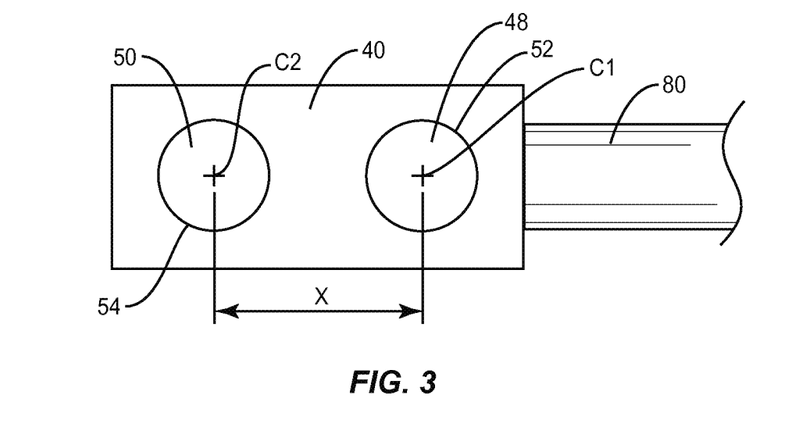
FIG. 3 is a break away view of the components shown in FIG. 2.

The following discussion includes a description of a surgical system and related methods of employing the surgical system. Alternate embodiments are also disclosed. Reference is made in detail to the exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal construct, as described herein, may be formed substantially of biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal construct by application of a porous or semi-porous coating of titanium.

Figure 4:
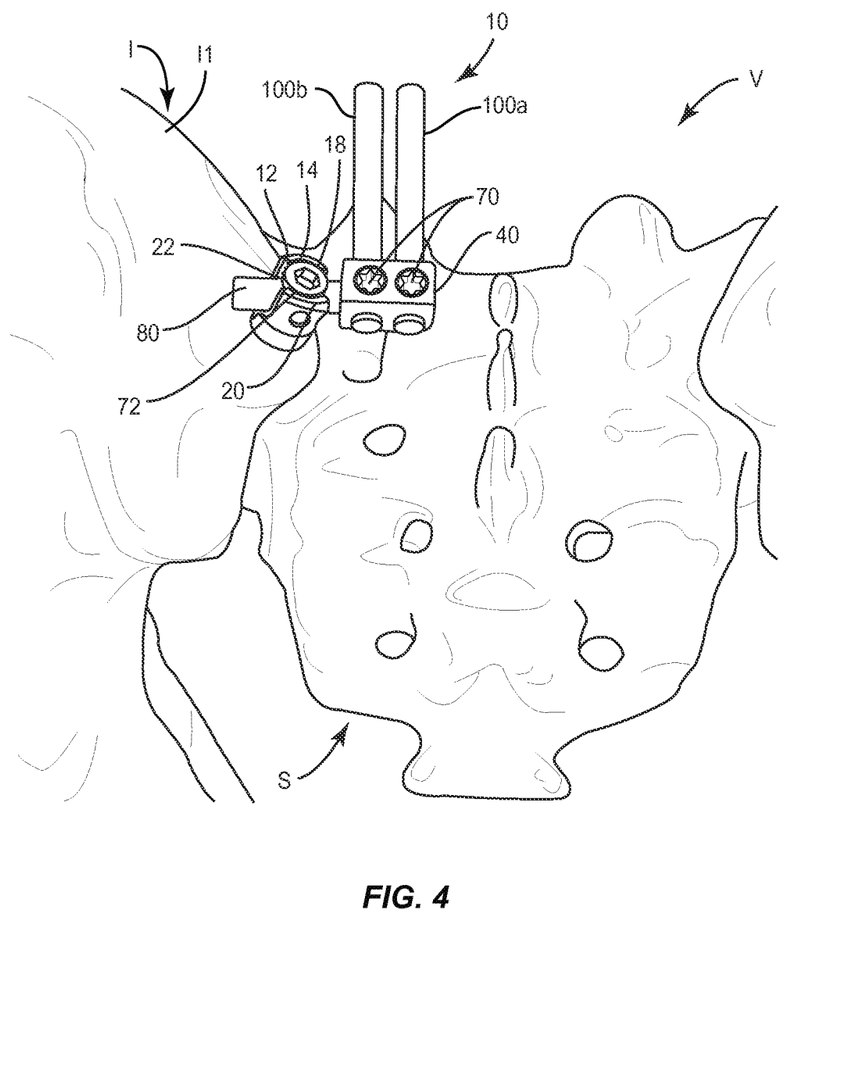
FIG. 4 is a perspective view of the components shown in FIG. 1 disposed with a body.
Figure 5:
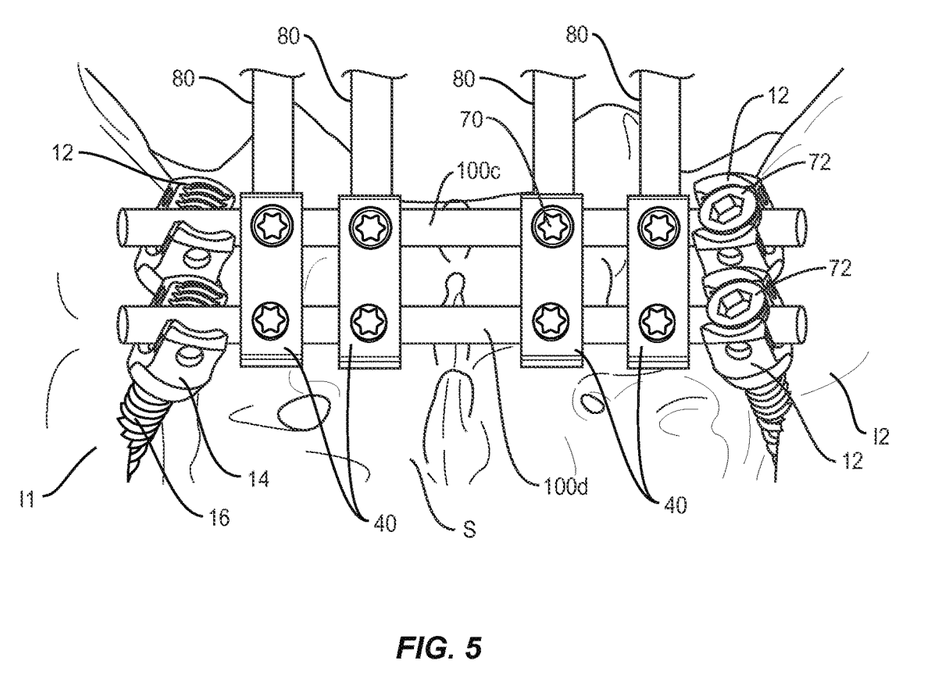
FIG. 5 is a perspective view of components of one embodiment of a system in accordance with the principles of the present disclosure disposed with a body.

Spinal implant system 10 may be employed, for example, with minimally invasive procedures, including percutaneous techniques, mini-open surgical techniques and/or open surgical techniques to deliver and introduce instrumentation and/or implants, such as, for example, a spinal construct, at a surgical site within a subject body of a patient, which includes, for example, a spine having vertebrae V and an ilium I, as shown, for example, in FIGS. 4 and 5. In some embodiments, the spinal constructs can include one or more bone fasteners, spinal rods, connectors and/or plates.

Spinal implant system 10 includes a spinal construct comprising a fastener 12. Fastener 12 includes a first portion, such as, for example, a receiver 14 and a second portion configured to penetrate tissue, such as, for example, a shaft 16, as shown in FIG. 3. Receiver 14 defines a longitudinal axis and includes a pair of spaced apart arms 18, 20 that each extend parallel to the longitudinal axis.

Arms 18, 20 define a U-shaped implant cavity 22 therebetween configured for disposal of a connector 40 of the spinal construct, as described herein. Cavity 22 extends perpendicular to the longitudinal axis of receiver 14. In some embodiments, cavity 22 may have various cross section configurations, such as, for example, oval, oblong, triangular, rectangular, square, polygonal, irregular, uniform, non-uniform, variable, tubular and/or tapered. In some embodiments, arm 18, arm 20 and/or cavity 22 may be disposed at alternate orientations, relative to the longitudinal axis of receiver 14, such as, for example, transverse, perpendicular and/or other angular orientations such as acute or obtuse, co-axial and/or may be offset or staggered. In some embodiments, receiver 14 may be closed to define a closed cavity 22. In some embodiments, a set screw may engage receiver 14 to fix and/or lock a spinal implant with receiver 14.

Shaft 16 is configured with a cylindrical cross section and includes an outer surface having an external thread form. In some embodiments, the thread form may include a single thread turn or a plurality of discrete threads. In some embodiments, the thread form may be self-tapping or intermittent, or may have more than one crest winding about shaft 16. In some embodiments, other engaging structures may be disposed on shaft 16, such as, for example, a nail configuration, barbs, expanding elements, raised elements and/or spikes to facilitate engagement of the shaft with tissue, such as, for example, vertebrae. In some embodiments, all or only a portion of shaft 16 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of the outer surface of shaft 16 may have alternate surface configurations to enhance fixation with tissue such as, for example, rough, arcuate, undulating, mesh, porous, semi-porous, dimpled and/or textured. In some embodiments, all or only a portion of shaft 16 may be cannulated.

Connector 40 extends between an end 42 and an end 44. Connector 40 includes a surface 46 that defines an implant cavity, such as, for example, a passageway 48 and an implant cavity, such as, for example, a passageway 50. Passageways 48, 50 are configured for disposal of implants, such as, for example, a spinal rods 100a, 100b. Connector 40 includes a continuous wall 52 that defines passageway 48 for disposal of spinal rod 100a. Connector 40 includes a continuous wall 54 that defines passageway 50 for disposal of spinal rod 100b. Continuous walls 52, 54 form a closed/closed connector configuration, as shown in FIG. 1.

Passageway 48 is spaced apart from passageway 50 such that a center C1 of passageway 48 is spaced a distance x from a center C2 of passageway 50. In one embodiment, passageways 48, 50 are disposed in a relatively parallel configuration, as shown in FIG. 1. In some embodiments, distance x can include a range of lengths to offset center C1 from center C2 for orientation of spinal rod 100a relative to spinal rod 100b.

In some embodiments, all or only a portion of passageway 48 and/or passageway 50 may have alternate cross section configurations, such as, for example, oval, oblong, triangular, square, polygonal, irregular, uniform, non-uniform, offset, staggered, undulating, arcuate, variable and/or tapered. In some embodiments, surface 46 may have alternate surface configurations to enhance fixation with spinal rod 100 such as, for example, rough, arcuate, undulating, mesh, porous, semi-porous, dimpled and/or textured.

Connector 40 includes a surface 60 that defines an opening 62a disposed in alignment with passageway 48. Opening 62a communicates with passageway 48. In some embodiments, opening 62a is in communication with passageway 50. Surface 60 defines an opening 62b disposed in alignment with passageway 50. Opening 62b communicates with passageway 50. In some embodiments, opening 62b is in communication with passageway 48.

Opening 62a is spaced apart from opening 62b, such as, for example, in a relatively parallel configuration. Opening 62a includes a threaded portion 64a and opening 62b includes a threaded portion 64b. Portions 64a, 64b are each configured for engagement with a lock, such as, for example, one or more set screws 70. A set screw 70 is engageable with portion 64a to selectively fix spinal rod 100a relative to connector 40 and a set screw 70 is engageable with portion 64b to selectively fix spinal rod 100b relative to connector 40, as described herein.

In some embodiments, all or only a portion of opening 62a and/or opening 62b may have alternate cross section configurations, such as, for example, oval, oblong, triangular, square, polygonal, irregular, uniform, non-uniform, offset, staggered, undulating, arcuate, variable and/or tapered. In some embodiments, surface 60 may have alternate surface configurations to enhance fixation with spinal rods 100a, 100b, such as, for example, rough, arcuate, undulating, mesh, porous, semi-porous, dimpled and/or textured. In some embodiments, surface 60 can include various lock elements, such as, for example, frictional engagement, mutual grooves, screws, adhesive, nails, barbs and/or raised elements.

Connector 40 includes a longitudinal element, such as, for example, a shaft 80. Shaft 80 extends between an end 82 and an end 84. End 82 is connected with end 44 of connector 40. In some embodiments, end 84 is configured for connection with receiver 14 of fastener 12. In some embodiments, end 84 is configured for connection with vertebrae via one or more fasteners.

Shaft 80 can have a uniform thickness/diameter. In some embodiments, shaft 80 may have various surface configurations, such as, for example, rough, threaded for connection with surgical instruments, arcuate, undulating, porous, semi-porous, dimpled, polished and/or textured. In some embodiments, the thickness defined by shaft 80 may be uniformly increasing or decreasing, or have alternate diameter dimensions along its length. In some embodiments, shaft 80 may have various cross section configurations, such as, for example, oval, oblong, triangular, rectangular, square, polygonal, irregular, uniform, non-uniform, variable and/or tapered.

In some embodiments, spinal rod 100a and/or spinal rod 100b may have a semi-rigid, rigid or elastic configuration, and/or have elastic properties, such as the elastic properties corresponding to the material examples described above. In some embodiments, spinal rod 100a and/or spinal rod 100b can include a plurality of separately attachable or connectable portions or sections, or may be monolithically formed as a single continuous element. The spinal construct can include one or a plurality of spinal rods. In some embodiments, spinal rod 100a and/or spinal rod 100b can be configured to extend over one or a plurality of vertebral levels.

Spinal rod 100a and/or spinal rod 100b can have a uniform thickness/diameter. In some embodiments, spinal rod 100a and/or spinal rod 100b may have various surface configurations, such as, for example, rough, threaded for connection with surgical instruments, arcuate, undulating, porous, semi-porous, dimpled, polished and/or textured. In some embodiments, the thickness defined by spinal rod 100a and/or spinal rod 100b may be uniformly increasing or decreasing, or have alternate diameter dimensions along its length. In some embodiments, spinal rod 100a and/or spinal rod 100b may have various cross section configurations, such as, for example, oval, oblong, triangular, rectangular, square, polygonal, irregular, uniform, non-uniform, variable and/or tapered.

In one embodiment, connector 40 is laterally oriented and a medial spinal rod 100a is configured for disposal in passageway 48 and a lateral spinal rod 100b is configured for disposal in passageway 50. In some embodiments, spinal rods 100a, 100b extend unilaterally relative to vertebrae V. In some embodiments, a plurality of connectors 40 are disposed in a bi-lateral orientation with vertebrae V.

In assembly, operation and use, spinal implant system 10, similar to the systems and methods described herein, is employed with a surgical procedure, as described herein, for treatment of a condition or injury of an affected section of the spine comprising vertebrae V, which may include sacrum S, and/or ilium I, as shown in FIG. 4. For example, components of system 10 such as one or more connectors 40, spinal rods 100a, 100b and/or bone fasteners 12 are employed with a surgical procedure for treatment of a spinal disorder affecting a section of the spine and/or ilium bones of a pelvis of a patient, as discussed herein.

In use, to treat the affected section of the spine, a medical practitioner obtains access to a surgical site comprising vertebrae V including sacrum S and ilium I in any appropriate manner, such as through incision and retraction of tissues. Spinal implant system 10 may be used in any existing surgical method or technique including open surgery, mini-open surgery, minimally invasive surgery and percutaneous surgical implantation, whereby portions of vertebrae V including sacrum S and ilium I are accessed through one or more micro-incisions, or sleeves that provide a protected passageway to the area. Once access to the surgical site is obtained, the particular surgical procedure is performed for treating the spinal disorder. Spinal implant system 10 is employed to augment the surgical treatment. One or more of the components of system 10 can be delivered or implanted as a pre-assembled device or can be assembled in situ.

In one embodiment, bone fastener 12 is configured for fixation with an ilium surface I1 of ilium I. A pilot hole is made in ilium surface I1 for receiving bone fastener 12. Shaft 16 is inserted or otherwise connected to ilium surface I1. Rods 100a and 100b, as described herein, are connected with a lumbar and/or thoracic portion of vertebrae V via fasteners, similar to those described herein.

Shaft 80 is oriented for alignment and disposed with receiver 14 of bone fastener 12. A set screw 72 is engaged with receiver 14 to provisionally fix connector 40 with fastener 12. Connector 40 is connected with bone fastener 12 to provide selective positioning and/or translation of connector 40 and/or rods 100a, 100b in one or a plurality of orientations relative to vertebrae V, ilium I and/or bone fastener 12 disposed with tissue. In some embodiments, connector 40 may be rotated relative to tissue, rotated about its own axis, rotated relative to spinal rods 100a, 100b and/or translated laterally, axially or combinations thereof.

Rods 100a, 100b are selectively oriented for alignment and inserted into passageways 48, 50. In one embodiment, rods, 100a, 100b are disposed with passageways 48, 50 prior to connection of connector 40 with fastener 12. In some embodiments, connector 40 is manipulated, as described herein, into an orientation and alignment for receiving rods 100a, 100b. Spinal rods 100a, 100b are locked with connector 40 via set screws 70. Rods 100a, 100b are secured with connector 40 in fixed engagement and uni-laterally disposed with vertebrae V. Set screw 72 is tightened to lock connector 40 with fastener 12. In some embodiments, a plurality of connectors 40 can be connected with a plurality of bone fasteners 12 and secured with a plurality of rods 100a, 100b in a bi-lateral configuration with vertebrae V.

In one embodiment, as shown in FIG. 5, bone fasteners 12 are configured for fixation with a sacro-iliac region and/or sacro-iliac joints, which include ilium surfaces I1, I2 and sacrum S. Pilot holes are made in tissues of the sacro-iliac joints and the sacro-iliac region including ilium surfaces I1, I2 and sacrum S for receiving bone fasteners 12. Shafts 16 are inserted or otherwise connected to the sacro-iliac region.

A plurality of connectors 40 are disposed adjacent sacrum S and manipulated, as described herein, into an orientation and alignment such that shafts 80 are attached with a lumbar and/or thoracic portion of vertebrae V via fasteners, similar to those described herein. In some embodiments, one or more connectors 40 are disposed in a relatively parallel orientation. In some embodiments, one or more connectors 40 may be disposed in other relative orientations, such as, for example, transverse, offset, staggered and/or angular. Connectors 40 are connected with vertebrae V in a bi-lateral configuration, two connectors 40 disposed with a lateral side of vertebrae V and two connectors 40 disposed with a contra-lateral side of vertebrae V. Passageways 48, 50 are oriented laterally or transverse relative to vertebrae V and across sacrum S.

Rods 100c, 100d, similar to the spinal rods described herein, are selectively oriented for alignment and inserted into passageways 48, 50 of each of connectors 40 in a trans-sacral orientation. Spinal rods 100c, 100d are provisionally fixed to connectors 40 via set screws 70. Spinal rods 100c, 100d are connected with bone fasteners 12 to provide selective positioning and/or translation of connectors 40 and/or rods 100c, 100d in one or a plurality of orientations relative to vertebrae V, surfaces I1, I2 and/or bone fasteners 12 disposed with tissue. In some embodiments, one or more connectors 40 may be rotated relative to tissue, about their own axes, rotated relative to spinal rods 100c, 100d and/or translated laterally, axially or combinations thereof.

Spinal rods 100c, 100d are oriented for alignment and disposed with receivers 14 of bone fasteners 12. Set screws 72 are engaged with receivers 14 to provisionally fix spinal rods 100c, 100d with bone fasteners 12. Upon selected positioning of spinal rods 100c, 100d and connectors 40 with bone fasteners 12 and/or tissue, set screw 72 is tightened to lock spinal rods 100c, 100d with fasteners 12.

Upon completion of the procedure, the surgical instruments, assemblies and non-implanted components of spinal implant system 10 are removed and the incision is closed. Spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, the fasteners may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 6:
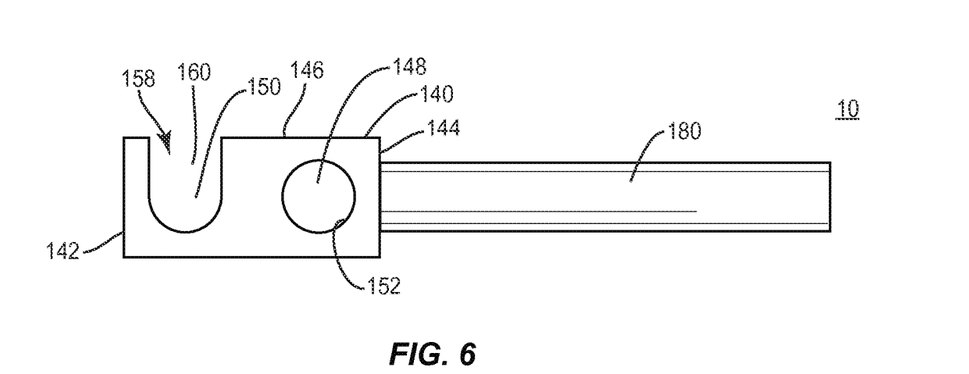
FIG. 6 is a side view of components of one embodiment of a system in accordance with the principles of the present disclosure.

In one embodiment, as shown in FIG. 6, spinal implant system 10, similar to the systems and methods described herein, includes a connector 140 having a closed/open connector configuration. Connector 140 extends between an end 142 and an end 144 and includes a shaft 180, similar to shaft 80 described herein. Connector 140 includes a surface 146 that defines a passageway 148 and a passageway 150. Passageways 148, 150 are configured for disposal of spinal rods, as described herein. Surface 146 includes a wall 152 that defines a passageway 148. Passageway 150 comprises a U-shaped cavity 158 having an opening 160 oriented to receive a spinal rod.

Figure 7:
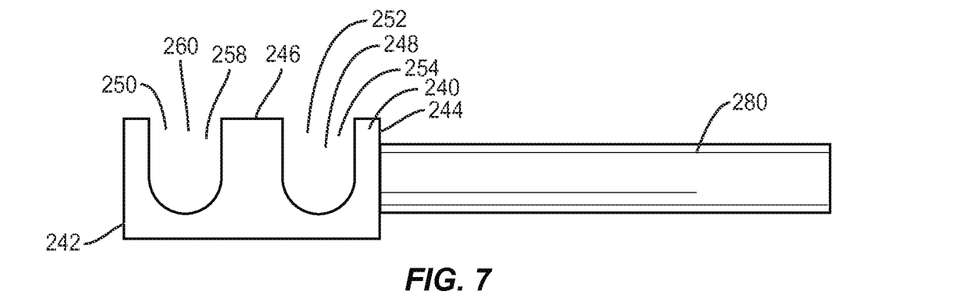
FIG. 7 is a side view of components of one embodiment of a system in accordance with the principles of the present disclosure.

In one embodiment, as shown in FIG. 7, spinal implant system 10, similar to the systems and methods described herein, includes a connector 240 having an open/open connector configuration. Connector 240 extends between an end 242 and an end 244 and includes a shaft 280, similar to shaft 80 described herein. Connector 240 includes a surface 246 that defines passageways 248, 250 configured for disposal of spinal rods, similar to that described herein. Passageway 248 comprises a U-shaped cavity 252 having an opening 254 oriented to receive a spinal rod. Passageway 250 comprises a U-shaped cavity 258 having an opening 260 oriented to receive a spinal rod.

Figure 8:
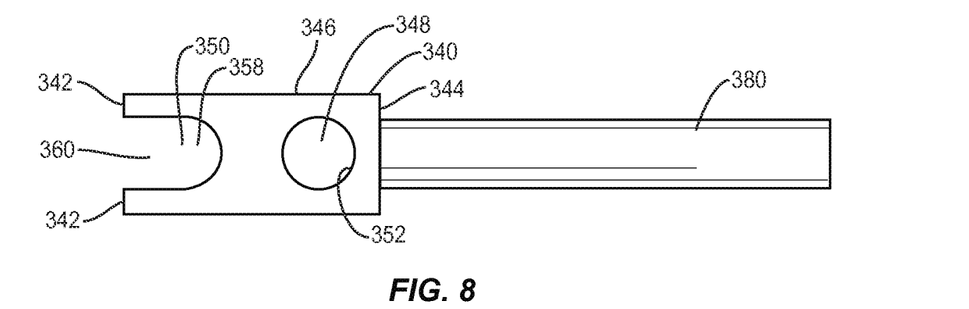
FIG. 8 is a side view of components of one embodiment of a system in accordance with the principles of the present disclosure.

In one embodiment, as shown in FIG. 8, spinal implant system 10, similar to the systems and methods described herein, includes a connector 340 having closed/side load connector configuration. Connector 340 extends between an end 342 and an end 344 and includes a shaft 380, similar to shaft 80 described herein. Connector 340 includes a surface 346 that defines passageways 348, 350 configured for disposal of spinal rods, as described herein. Surface 346 includes a wall 352 that defines passageway 348. Passageway 350 comprises a U-shaped cavity 358 having an opening 360 oriented to receive a spinal rod.

Figure 9:
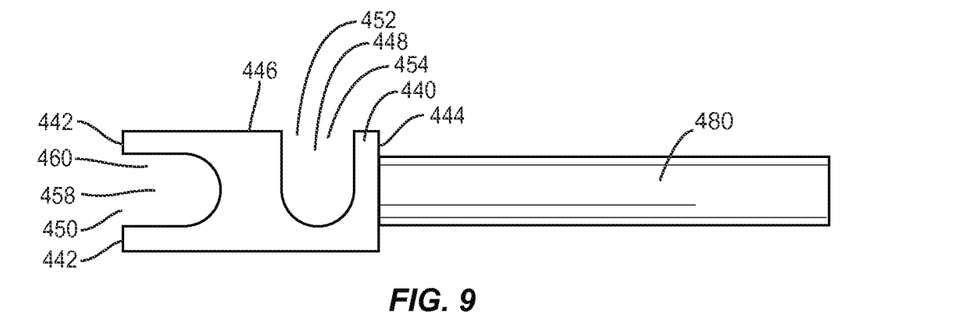
FIG. 9 is a side view of components of one embodiment of a system in accordance with the principles of the present disclosure.

In one embodiment, as shown in FIG. 9, spinal implant system 10, similar to the systems and methods described herein, includes a connector 440 having an open/side load connector configuration. Connector 440 extends between an end 442 and an end 444 and includes a shaft 480, similar to shaft 80 described herein. Connector 440 includes a surface 446 that defines passageways 448, 450 configured for disposal of spinal rods, as described herein. Passageway 448 comprises a U-shaped cavity 452 having an opening 454 oriented to receive a spinal rod. Passageway 450 comprises a U-shaped cavity 458 having an opening 460 oriented to receive a spinal rod.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a fastener attachable with sacral and/or pelvic tissue of a body, the fastener includes a threaded shaft and a receiver connected to the threaded shaft, the receiver comprising a pair of spaced apart arms that defines a rod cavity therebetween;
   at least one connector being connected with the fastener and defining a first implant cavity and a second implant cavity, the at least one connector including a longitudinal portion extending therefrom, the longitudinal portion being configured for disposal within the rod cavity; and
   at least one lock disposable with the implant cavities.

2. A spinal construct as recited in claim 1, wherein the cavities are spaced apart.

3. A spinal construct as recited in claim 1, wherein the cavities are disposed in a relatively parallel orientation.

4. A spinal construct as recited in claim 1, wherein the at least one lock includes a first set screw disposable with the first implant cavity and a second set screw disposable with the second implant cavity.

5. A spinal construct as recited in claim 1, wherein the at least one lock engages an implant positioned within one of the implant cavities to selectively position the implant relative to the at least one connector.

6. A spinal construct as recited in claim 1, further comprising a first spinal rod disposed in the first cavity and a second spinal rod disposed in the second cavity.

7. A spinal construct as recited in claim 1, wherein the at least one connector includes at least one lateral connector and at least one contra-lateral connector.

8. A spinal construct as recited in claim 1, wherein:
the first implant cavity extends along a first longitudinal axis;
the second implant cavity extends along a second longitudinal axis that extends parallel to the first longitudinal axis; and
the longitudinal portion extends along a third longitudinal axis that extends transverse to the first and second longitudinal axes.

9. A spinal construct as recited in claim 1, wherein:
the first implant cavity extends along a first longitudinal axis;
the second implant cavity extends along a second longitudinal axis; and
the longitudinal portion extends along a third longitudinal axis that intersects the first and second longitudinal axes.

10. A spinal construct as recited in claim 1, wherein the longitudinal portion includes a shaft having a cylindrical configuration.

11. A spinal construct as recited in claim 10, wherein the shaft is free of any openings.

12. A spinal construct as recited in claim 1, wherein:
the connector extends between opposite top and bottom surfaces, the top and bottom surfaces each extend between opposite front and back surfaces, and the top and bottom surfaces and the front and back surfaces each extend between first and second side surfaces; and
the first and second implant cavities each extend through the front and back surfaces without extending through the bottom surface or the side surfaces.

13. A spinal construct as recited in claim 1, wherein:
the connector extends between opposite top and bottom surfaces, the top and bottom surfaces each extend between opposite front and back surfaces, and the top and bottom surfaces and the front and back surfaces each extend between first and second side surfaces;
the first implant cavity extends through the front and back surfaces without extending through the bottom surface or the side surfaces; and
the second implant cavity extends through the front surface, the back surface and the top surface without extending through the bottom surface or the side surfaces.

14. A spinal construct as recited in claim 1, wherein:
the connector extends between opposite top and bottom surfaces, the top and bottom surfaces each extend between opposite front and back surfaces, and the top and bottom surfaces and the front and back surfaces each extend between first and second side surfaces; and
the first and second implant cavities each extends through the front surface, the back surface and the top surface without extending through the bottom surface or the side surfaces.

15. A spinal construct as recited in claim 1, wherein:
the connector extends between opposite top and bottom surfaces, the top and bottom surfaces each extend between opposite front and back surfaces, and the top and bottom surfaces and the front and back surfaces each extend between first and second side surfaces;
the first implant cavity extends through the front and back surfaces without extending through the bottom surface or the side surfaces; and
the second implant cavity extends through the front surface, the back surface and the first side surface without extending through the top surface, the bottom surface or the second side surface.

16. A spinal construct as recited in claim 1, wherein:
the connector extends between opposite top and bottom surfaces, the top and bottom surfaces each extend between opposite front and back surfaces, and the top and bottom surfaces and the front and back surfaces each extend between first and second side surfaces;
the first implant cavity extends through the front surface, the back surface and the first side surface without extending through the top surface, the bottom surface or the second side surface; and
the second implant cavity extends through the front and back surfaces without extending through the bottom surface or the side surfaces.

17. A spinal construct as recited in claim 1, wherein the implant cavities each have a uniform diameter.

18. A spinal construct as recited in claim 1, further comprising set screws, wherein the connector comprises a first opening that is in communication with the first implant cavity and a second opening that is communication with the second implant cavity, the openings being configured for disposal of one of the set screws.

19. A spinal construct comprising:
a fastener attachable with sacral and/or pelvic tissue of a body;
at least one connector defining a first cavity extending along a first longitudinal axis and a second cavity extending along a second longitudinal axis, the at least one connector including a longitudinal portion connectable to the fastener, the longitudinal portion extending along a third longitudinal axis that extends transverse to the first and second longitudinal axes;
first and second spinal rods connected with vertebral tissue of the body and disposable within the cavities; and
first and second locks disposable with the cavities and engageable with the spinal rods to selectively position the spinal rods relative to the at least one connector.

20. A spinal construct comprising:
a plurality of fasteners attachable with sacral and/or pelvic tissue of a body, the fasteners each having a threaded shaft and a receiver connected to the threaded shaft, the receiver comprising a pair of spaced apart arms that defines an implant cavity therebetween;
at least one connector defining a first cavity and a second cavity, the at least one connector including a longitudinal portion configured for disposal in at least one of the implant cavities;
trans-sacral rods that are each connected with at least one of the fasteners and disposable within one of the cavities; and
first and second locks disposable with the first and second cavities and engageable with the trans-sacral rods to selectively position the at least one connector relative to the trans-sacral rods.

* * * * *

UNITED STATES PATENT AND TRADEMARK OFFICE
CERTIFICATE OF CORRECTION

PATENT NO. : 9,763,695 B2  
APPLICATION NO. : 14/541900  
DATED : September 19, 2017  
INVENTOR(S) : Mirda It is certified that error appears in the above-identified patent and that said Letters Patent is hereby corrected as shown below:

In the Specification

In Column 1, Line 14, delete "hemiation," and insert -- herniation, --, therefor.

In Column 3, Line 36, delete "dearly" and insert -- clearly --, therefor.

In Column 9, Line 45, delete "dips," and insert -- clips --, therefor.

Signed and Sealed this  
Thirteenth Day of March, 2018

Andrei Iancu  
*Director of the United States Patent and Trademark Office*